United States Patent [19]

Lund

[11] Patent Number: 4,486,610
[45] Date of Patent: Dec. 4, 1984

[54] PURIFICATION OF 2,4,4'-TRICHLORO-2'-HYDROXYDIPHENYLETHER SOLVENT EXTRACTION

[75] Inventor: Richard B. Lund, Jackson, Ala.

[73] Assignee: Ciba-Geigy Corporation, Ardsley, N.Y.

[21] Appl. No.: 464,531

[22] Filed: Feb. 7, 1983

[51] Int. Cl.³ .............................................. C07C 41/38
[52] U.S. Cl. .................................... 568/637; 549/460
[58] Field of Search ......................... 568/637; 549/460

[56] References Cited

U.S. PATENT DOCUMENTS 4,268,693 5/1981 Muntwyler et al. ................. 568/637
4,355,186 10/1982 Becker et al. .................. 568/637 X Primary Examiner—Bernard Helfin
Attorney, Agent, or Firm—Karl F. Jorda

[57] ABSTRACT

A process is described for purifying the bacteriostat 2,4,4'-trichloro-2'-hydroxydiphenylether prepared by the diazotization of 2,4,4'-trichloro-2'-aminodiphenylether from the 2,4,8-trichlorodibenzofuran and associated nonphenolics which form. A selective solvent extraction for these non-phenolics consisting of tetrachlorethylene is used after neutralization of the hydrolyzed diazo product.

6 Claims, No Drawings

PURIFICATION OF 2,4,4'-TRICHLORO-2'-HYDROXYDIPHENYLETHER SOLVENT EXTRACTION

FIELD OF THE INVENTION

This invention relates to the synthesis of 2,4,4'-trichloro-2'-hydroxydiphenylether, a bacteriostat useful in the formulation of cosmetics and soaps. More particularly, this invention, in the synthesis of said 2,4,4'-trichloro-2'-hydroxydiphenylether by diazotization, relates more specifically to the removal of impurities arising from said synthesis.

BACKGROUND OF THE INVENTION

The bacteriostat 2,4,4'-trichloro-2'-hydroxydiphenylether, covered by U.S. Pat. No. 3,506,720, is annually marketed in million-pound quantities under the trademark IRGASAN DP-300 ® for use in soaps and cosmetics. It has been produced from 2,4,4'-trichloro-2-aminodiphenylether (TADE) by diazotization and hydrolysis according to Equation 1:

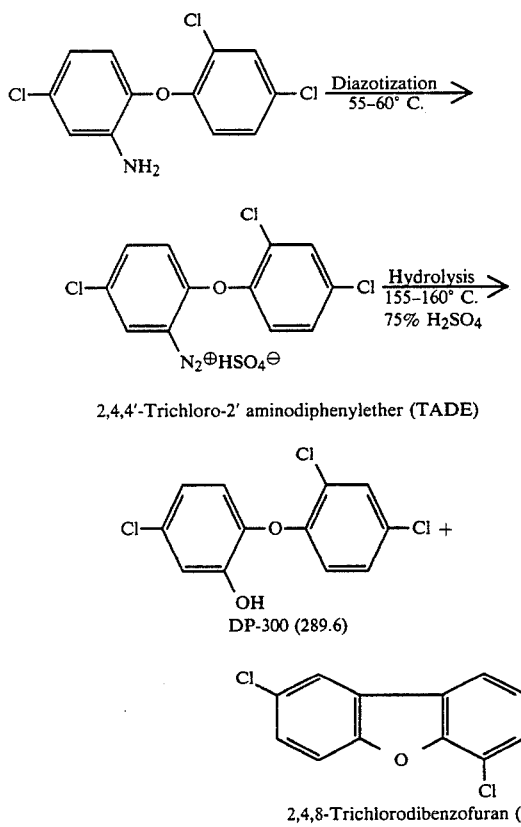

Products of this synthesis, in addition to the desired phenol (DP-300), include 24–28% 2,4,8-trichlorodibenzofuran (TCDBF) and traces of more than ten other compounds including phenolics and non-phenolics related to or derived from the furan compound.

Because of strict cosmetic industry and FDA specifications, the products of the above synthesis have required extensive and intensive purification procedures including high-vacuum distillation, precipitation, filtration and solvent recrystallization leaving a yield (based on TADE) of about 53.5% IRGASAN DP-300.

The major compounds found as impurities in the synthesis according to Equation 1 and their concentration limits in the commercial product are as follows:

| | |
|---|---|
| 2,4-Dichlorophenol (2,4-DCP) | <0.01% |
| 4-Chlorophenol (4-CP) | <0.01% |
| 4,4-Dichloro-2-hydroxydiphenylether (DCHDPE) | <0.7% |
| 2,4,8-Trichlorodibenzofuran (TCDBF) | <10 ppm |
| 2,8-Dichlorodibenzofuran (DCDBF) | <1 ppm |

In the previous procedures, these standards of purity were achieved by diazotizing molten 2,4,4'-trichloro-2'-aminodiphenylether with nitrosyl sulfuric acid/sulfuric acid at 55°–60° C. The diazotization reaction mass was hydrolyzed by 75% sulfuric acid at 155°–160° C. The organic phase was separated from the acid at about 120° C. The organic (upper) phase was adjusted to pH >12 with 50% caustic to form a slurry containing the water-soluble sodium salt of IRGASAN DP-300 and precipitated furan (TCDBF). The slurry was filtered to remove most of the furan by-product. The alkaline filtrate was extracted with toluene to remove most of the associated non-phenolic impurities and then the product was acidified to form an oily lower organic phase containing the crude product and an aqueous phase containing some of the phenolic impurities. The organic phase was distilled, separating the fore run containing phenolic impurities up to 180° C./1 mm from the main cut at 180°–225° C./1 mm. The main cut of distilled IRGASAN DP-300 was recrystallized from an aliphatic petroleum solvent (NAPHTHOLITE 66/3) boiling in the range 130°–138° C. to yield a product meeting the above noted purity specifications. It is a slightly yellow crystalline material with a phenolic odor.

THE INVENTION

As a result of a review and study of the above noted previous procedures, it was found that the process for preparing and isolating 2,4,4'-trichloro-2'-hydroxydiphenylether could be vastly simplified to yield a product meeting commercial standards if the process, comprising the steps of diazotizing and hydrolyzing 2,3,4'-trichloro-2'-aminodiphenylether to form an aqueous mixture of said hydroxyether and 2,4,8-trichlorodibenzofuran and other chlorinated phenolic and non-phenolic by-products, included the improvement comprising the steps of separating said hydroxydiphenylether from said dibenzofuran and associated other non-phenolic impurities by contacting and extracting said furan and other non-phenolics from said aqueous hydrolysis mixture with a polychlorinated lower aliphatic hydrocarbon or a (chlorinated) aromatic hydrocarbon solvent, thus leaving said aqueous solution containing substantially said hydroxydiphenylether freed from non-phenolic impurities.

In extracting the furan and other non-phenolic impurities which are present in amounts of about 25 wt% of the reaction products and for which there is no present use, it is useful to initially convert the desired phenolic product to its alkali metal salt by alkalizing the hydrolysis mixture with an appropriate alkali hydroxide to pH greater than about 12. Dissolved caustic soda 50% is preferred on a cost basis but KOH may also be used.

Among the polychlorinated aliphatic hydrocarbon solvents suitable for the selective extraction and separation, those having 1 to 3 carbon atoms, such as, methylene chloride tetrachloroethane, ethylenedichloride, etc. as well as such aromatic hydrocarbon solvents as toluene chlorotoluene, dichlorobenzene, etc. are satisfactory. For best performance the solvent chosen should be immersible with water, inert to sulfuric acid and sodium hydroxide and capable of dissolving the impurities formed. Tetrachlorethylene ($Cl_2CH=CHCl_2$—TCE is preferred as extractant as it is the least toxic and has a convenient boiling range.

It must be noted that the furan, trichlorodibenzofuran, and the other non-phenolics have no present commercial use and thus are to be incinerated. In addition, the tetrachlorethylene (perchlorethylene) is an inexpensive useful non-flammable solvent which should be recovered as it would interfere with proper incineration. It is easily distilled from the non-phenolic impurities including the furan as it boils at 120°–121° C. It is relatively non-toxic when compared to the other polychlorinated aliphatic solvents useful for the extraction-separation.

Tetrachlorethylene is a liquid of high density (1.62 g/ml at 20° C.) which makes proper and vigorous agitation advisable to ensure efficient contact between the liquids for extraction and removal of the furan and non-phenolic impurities from the aqueous solution of the sodium salt of 2,4,4'-trichloro-2-hydroxydiphenylether.

To ensure rapid extraction by the tetrachlorethylene of the furan and non-phenolics from the aqueous solution of the sodium salt, it is advantageous to heat the agitated mixture to the range of about 70°–80° C. at which temperature the solubility of the impurities in the tetrachlorethylene is very rapid. The bulk of the 2,4,8-trichlorodibenzo furan is removed during the first extraction with tetrachlorethylene. However, to ensure removal of the trace non-phenolics to the low levels mandated by the commercial and FDA specifications, at least three and preferably five repeated tetrachlorethylene extractions are desirable.

The temperatures and agitation during these subsequent extractions need not be rigorously maintained.

The extraction contact time for the initial and subsequent extraction stages is governed by the temperature, agitation rates and the geometry of the extraction vessel.

As the 2,4,4'-trichloro-2'-aminodiphenylether is highly colored, the aqueous hydrolysis products from the diazotization are also highly colored. Thus the initial tetrachlorethylene extract is also colored and visual detection of the phase change areas and the interface between the phases is difficult. A phase-change indicating device is recommended for use during the decanting or separating of the extracts from the extracted materials. During the later separation stages this is not as critical, as substantially all the interfering color is removed by the first extraction.

A major advantage of the present solvent extraction procedure is that a costly labor-intensive filtration step involving expensive filtration equipment is avoided, with very significant savings.

In addition, the solvent extraction has been found to be more effective in the separation of the impurities, thus putting less of a strain upon control of the final distillation for ultimate clean-up of impurities. The final product thus easily exceeded the FDA and industry mandated specifications.

DETAILED DESCRIPTION

The invention will be more fully set forth in the appended examples detailing several laboratory procedures, and a full scale plant run. While several equipment, reagent, and reaction condition details are set forth, art-recognized equivalents thereof may be substituted where they do not depart from the scope and intent of the invention which is based upon the separation of the product from by-products and impurities by the recited class of solvents.

EXAMPLE 1

Methylene Dichloride Extractant Laboratory

A two-liter reaction vessel fitted with a heating jacket, stirring paddles, inlet tubes and thermometer wells is charged with 540 gm of 98% $H_2SO_4$ and 636 gm of $NOHSO_4$ (2 moles). The mixture is heated to 55° C. and 577 gm of 2,4,4'-trichloro-2'-aminodiphenylether (TADE) is slowly added. When addition is complete, additional $NOHSO_4$ is added until a positive nitrite test is obtained (to ensure completion of the diazotization). The reaction mixture is permitted to cool overnight with the agitation continued. The next morning this reactor is charged with 246 gm $H_2O$ and heated to 55°–60° C. A 3-liter reactor, fitted with a water cooled condenser is charged with 272 gm $H_2SO_4$ and 78 gm water and heated to 155°–160° C. The contents of the first reaction vessel is added over 3 hours to the second vessel and heating is continued at about 60° C. until the mixture gives a negative R-salt diazo test. The mixture is then cooled to 60°–70° C. One liter of methylene dichloride ($CH_2Cl_2$) is added to the contents of this reactor. Some of the $CH_2Cl_2$ is lost thru the condenser. The mixture is then permitted to cool. The lost $CH_2Cl_2$ is replaced and the mixture agitated. Then mixing is stopped and the phases are permitted to separate. The layers are split to yield 1750 gm of aqueous acid layer and 1610 gm of product in the organic layer. The organic layer is added to 2 liters of water and 135 gm of 50% aqueous NaOH, and mixed. The resultant slurry is filtered and 120 gm of furan is removed. The pH of the aqueous layer is adjusted to 9.5 and the layers are split. 2340 gm of aqueous layer and 457 gm crude product are separated. The latter is distilled to yield 298.9 gm (100%)=51.6% yield 99.6% pure. 2,4,4'-trichloro-2-hydroxydiphenylether (IRGASAN DP-300).

EXAMPLE 2

TCE-Extractant Laboratory

A 2-liter bottom outlet reactor fitted with condenser, heater/cooling bath, thermometer and addition-ports is charged with 540 gm $H_2SO_4$ 98% and 636 gm $NOHSO_4$ (2 moles). To this mixture is added 577 gm TADE. Enough $NOHSO_4$ is added to give a positive nitrate test. A second similar reactor is charged with 272 gm $H_2SO_4$ and 78 gm water and the contents heated to 155°–160° C. The contents of the first reactor were diluted with 246 gm $H_2O$ and slowly charged over 2 hours into the acid mixture in the second reactor. Upon completion of the addition of the diazotized mixture, the heating was maintained at 160° C. until the mixture yielded a negative R-salt diazo test. The mixture was cooled to 120° C. and 1000 gm of tetrachlorethylene (TCE) was added to the acidic mixture. The two components were vigorously mixed for 30 minutes and then cooled to 90° C. The mixing was stopped and the two phases were chilled, separated and then split. The volumes of the two phases were substantially equal (1050 ml), the acid phase weighed 1692 gm and the organic phase weighed 1523 gms. The acid layer was re-extracted with two 200 ml portions of TCE which were combined with the previous TCE extract. The acid phase was then discarded, the organic phase was then added to 1916 gm $H_2O$ and 135 gm NaOH (50%) in a 4 liter reactor and stirred at 70° C. for ½ hour. After agitation was discontinued the two layers were split. The TCE contained the impurities and the aqueous layer contained the crude product. The TCE layer upon cooling deposited solids; total weight including washes 1775 gm. The aqueous phase 2387 gm was introduced into a 5-neck 3-liter flask and adjusted to pH 9.35. Two layers separated, a product layer weighing 365.7 gm and an aqueous layer. The aqueous layer was acidified to pH 6.5 and extracted with 200 gm TCE. 202.8 gm of extract was collected. The product layer was introduced into a vacuum still and distilled at 200–225 and 5 mm. No fore run is collected. The main cut, 276.5 gm which is adjusted for samples to 279.2 gm—48% yield of 99.5% purity.

EXAMPLE 3

TCE Extractant Plant Scale

Into a 3000 gal. glass-lined vessel, fitted with a reflux condenser and stirrer is charged 82 gal. $H_2O$ and 181 gal of $H_2SO_4$ 93%. This mixture is heated to 155°–160° C. and 1544 gal of diazotized TADE mixture is added. The mixture is stirred and refluxed at 155°–160° C. for one hour or until the R-salt diazo test is negative. The mixture is then cooled to 120°–125° C. Agitation is stopped and the two layers allowed to separate for 45 minutes. These are an oily layer and an aqueous acidic layer with a combined volume of 1820 gal. The lower acid layer, 1315 gal, is split off. The remaining oily layer, 505 gal is transferred to a 3000 gal stainless steel vessel. To this transferred oily layer is added 513 gal of TCE and 1661 gal of water and the mixture is heated to 70°–80° C. with agitation. At about 70° C., 209 gal of 50% NaOH solution is added to adjust the mixture to pH 12–13. The mixture, 2896 gal, is agitated at 80° C. for 30 minutes and then agitation is discontinued. Between about 45–60 minutes separation of the layers is essentially complete. The lower TCE layer containing the "Furan" is split off—688 gal—and directed to TCE recovery plant. The furan and associated non-phenolic residues from TCE recovery are incinerated.

The aqueous "product" layer, 2,208 gal, is then vigorously mixed with 110 gal of TCE at 50° C.–70° C. for 30 minutes. The mixture (2318 gal) is then allowed to separate into two layers. The lower TCE layer is split off and directed to the solvent recovery facility. The extraction with agitation and separation is repeated with 4 additional portions (110 gal each) of TCE. These extracts are similarly directed to solvent recovery.

To the remaining aqueous product layer is added 19 gal of TCE and about 56 gal of $H_2SO_4$ 93%, sufficient to adjust the solution to about pH-7. The mixture (2304 gal) is stirred at 50°–70° C. for 30 minutes and then the resulting layers are allowed to settle for 45 minutes. The lower product layer, 357 gal, is transferred to a stripping still for product recovery. The upper aqueous layer, 1934 gal, is transferred to an acid recycle facility or for effluent treatment. The product layer is distilled to 150 C./50 mm until the volatile content is less than 1%. The distillate of $TCE/H_2O/$ and phenolics 188 gal is transferred to solvent recovery. The residue in this still, 1300 gal, is transferred to a molecular still to recover 15,444 lbs of 2,4,4'-trichloro-2'-hydroxydiphenylether, IRGASAN DP-300, the desire product.

What is claimed is:

1. In the process for preparing and isolating 2,4,4'-trichloro-2'-hydroxydiphenylether which comprises the steps of diazotizing and hydrolyzing 2,4,4'-trichloro-2'-aminodiphenylether to form an aqueous mixture of said hydroxyether and 2,4,8-trichlorodibenzofuran and other chlorinated by-products, the improvement which includes the steps of separating said hydroxydiphenyl ether from said dibenzofuran and said other non-phenolics by extracting same from said aqueous mixture by dissolving said furan and other non-phenolics in a polychlorinated lower aliphatic hydrocarbon solvent of 3 or less carbon atoms or an aromatic or chlorinated aromatic hydrocarbon solvent and leaving an aqueous solution of substantially 2,4,4'-trichloro-2-hydroxyphenyl ether as sodium salt.

2. The process according to claim 1 wherein said polychlorinated lower aliphatic hydrocarbon of 3 or less carbon atoms is selected from the group consisting of methylene chloride and tetrachlorethylene.

3. The process according to claim 2 wherein said polychlorinated hydrocarbon is tetrachlorethylene.

4. The process according to claim 3 wherein said separation and extraction steps include contacting and extracting the hydrolyzed mixture with said tetrachlorethylene at temperatures in the range 60°–100° C. to extract said "furan" by-products and impurities.

5. The process according to claim 4 wherein said contacting and extracting of the hydrolysis mixture with tetrachlorethylene is repeated at least 3 times.

6. The process according to claim 4 wherein said hydrolysis mixture, when in contact with said tetrachlorethylene, is alkalized to pH above about 11.

* * * * *